United States Patent
Anderson et al.

(12)

(10) Patent No.: US 6,248,341 B1
(45) Date of Patent: Jun. 19, 2001

(54) METHOD OF TREATING TOPICAL ANGIOGENESIS-RELATED DISORDERS

(75) Inventors: Jon Anderson, Galesburg, MI (US); Mary Steidl Matsui, Teaneck, NJ (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/483,952

(22) Filed: Jan. 14, 2000

(51) Int. Cl.$^7$ .................... A61K 6/00; A61K 7/00
(52) U.S. Cl. ............... 424/401; 424/78.02; 424/78.05; 424/195.1; 514/863; 514/886; 514/887
(58) Field of Search ................. 424/401, 195.1, 424/78.02, 78.05; 514/863, 886, 887

(56) References Cited

U.S. PATENT DOCUMENTS

| | | | |
|---|---|---|---|
| 5,306,486 | * | 4/1994 | McCook et al. ............... 424/59 |
| 5,605,929 | * | 2/1997 | Liao et al. ...................... 514/456 |
| 5,616,332 | * | 4/1997 | Herstein ......................... 424/401 |
| 5,670,154 | | 9/1997 | Hara et al. . |

FOREIGN PATENT DOCUMENTS

| | | |
|---|---|---|
| 4027350 | 3/1992 | (DE) . |
| 4138192 | 5/1993 | (DE) . |
| 2293548 | 4/1996 | (GB) . |
| 52136909 | 11/1977 | (JP) . |
| 06024954 | 2/1994 | (JP) . |
| 06199646 | 7/1994 | (JP) . |
| 07025742 | 1/1995 | (JP) . |
| 10101624 | 4/1998 | (JP) . |
| 9308763 | 9/1993 | (KR) . |
| WO 9414414 | 7/1994 | (WO) . |
| WO 96/23512 | * 8/1996 | (WO) . |
| 9628178 | 9/1996 | (WO) . |

OTHER PUBLICATIONS

Fotsis, et al., "Flavonoids, Dietary–derived Inhibitors of Cell Proliferation and in Vitro Angiogenesis", Cancer Research 57, pp. 2916–2921 (Jul. 15, 1997).

Cao, et al., "Angiogenesis Inhibited by Drinking Tea", Macmillan Magazines Ltd., (p. 381), Nature, vol. 398, Apr. 1, 1999, www.nature.com.

Kitano, et al., "Sealing Effects of (–)—Epigallocatechin Gallate on Protein Kinase C and Protein Phosphatase 2A", Biophysical Chemistry 65 (1997), pp. 157–164.

Jackson, et al., "The Role of Platelet Activating Factor and Other Lipid Mediators in Inflammatory Angiogenesis", Biochimica et Biophysica Acta 1392 (1998), pp. 145–152.

Jackson, et al., "Modulation of Angiogenesis in a Model of Chronic Inflammation", Inflammation Research 46, Supplement 2 (1997), pp. S129–S130.

Tsopanoglou, et al., "Protein Kinase C Involvement in the Regulation of Angiogenesis", Journal Vasc. Research 1993, 30: 202–208.

\* cited by examiner

*Primary Examiner*—James M. Spear
*Assistant Examiner*—Liliana Di Nola-Baron
(74) *Attorney, Agent, or Firm*—Kenyon & Kenyon

(57) ABSTRACT

The present invention relates to a method of inhibiting angiogenesis in mammalian tissue which comprises supplying to the tissue a composition comprising an effective amount of epigallocatechin-gallate, epicatechin gallate or a combination thereof. The method is particularly useful in the treatment of angiogenesis-related skin conditions in which the catechin is applied topically, such as the treatment of various skin cancers, psoriasis, spider veins or undereye circles.

10 Claims, No Drawings

METHOD OF TREATING TOPICAL ANGIOGENESIS-RELATED DISORDERS

FIELD OF THE INVENTION

The invention relates to cosmetic and pharmaceutical treatment methods. More specifically, the invention relates to treatment of angiogenesis-related disorders, particularly skin disorders.

BACKGROUND OF THE INVENTION

Angiogenesis, which is the process of producing new capillaries from already existing blood vessels, is a tightly regulated event that does not normally occur in healthy adults, except for certain very specific occurrences such as wound-healing and the female reproductive cycle. It is a complex process that involves a number of steps, including basement membrane degradation, cellular proliferation, migration, and differentiation of endothelial cells, formation of a lumen, and deposition of a new basement membrane. The regulation of the process is also complex, involving a number of diverse factors, for example, enzymes such as collagenase and protein kinase C, growth factors and signaling molecules such as VEGF and cAMP, and by cell-matrix adhesion molecules. Angiogenesis is an integral part of the pathogenesis of certain conditions, such as tumor formation, and chronic inflammatory disorders such as rheumatoid arthritis. Angiogenesis has been associated with chronic inflammatory skin diseases characterized by the neogenesis of capillaries and post-capillary venules due to over-expression of VEGF in epidermal keratinocytes. New vessel growth exacerbates chronic inflammation by facilitating infiltration of monocytes and lymphocytes. In addition to the angiogenic growth factors VEGF and FGF, the cytokines TNFA and IL-1, as well as the lipid inflammatory mediators $PGE_1$, $PGE_2$, and PAF have also been implicated in inflammatory angiogenesis. Because there are so many stages in the pathway, however, this provides a number of points in the pathway at which its progress can be stopped. A number of different natural sources of angiogenesis inhibitors have previously been reported; the present invention now presents a new natural source for limiting the progress of angiocenesis.

SUMMARY OF THE INVENTION

The invention relates to a method of inhibiting angiogenesis in a mammalian tissue which comprises providing to the tissue an effective amount of epigallocatechin gallate (EGCG), epicatechin gallate(ECG), or a combination thereof. The method can be used to treat a number of conditions, such as chronic inflammatory conditions and cancerous tumors. In a particularly preferred embodiment, the EGCG and/or ECG are applied topically to inhibit or reduce angiogenesis associated with various skin conditions.

DETAILED DESCRIPTION OF THE INVENTION

EGCG and ECG are two of several polyphenols that occur naturally in green tea, among other natural sources. These two compounds, and green tea generally, have found numerous cosmetic and pharmaceutical uses, including free-radical scavenging, skin whitening, antiinflammatory, and hair coloring. It has now been unexpectedly discovered that these compounds are capable of inhibiting the process of angiogenesis. In particular, it had been initially observed in vitro that each of these compounds can inhibit both collagenase and protein kinase C, as well as VEGF-induced migration of endothelial cells, some of the many components that are involved in the angiogenesis pathway. The effect of these inhibitions on angiogenesis has subsequently been confirmed in vivo in the chick embryo chorioallantoic membrane assay.

Although several flavonoid compounds have previously been shown to be active in inhibiting angiogenesis(Fotsis et al., Cancer Research 5: 2916–2921, 1997), it has been expressly noted that catechin was inactive in this regard. It is therefore particularly surprising to observe that these specific green tea catechins have any effect on angiogenesis. The catechins employed in the invention may be a EGCG or ECG-enriched fraction of green tea, or it can be any substantially pure EGCG, ECG, or combinations thereof, "substantially pure" being defined as at least 75%, preferably at least 90% free of non-EGCG or ECG compounds.

The effect on angiogenesis of EGCG and ECG is dose-dependent. When evaluated in the chorioallantoic membrane assay, which measures the inhibition of migration of endothelial cells, concentrations of as low as 0.01 mg/ml has a substantial effect on inhibiting this migration, this effect increasing as the concentration is increased, and being most pronounced at a level of about 1 mg/ml. Thus, for practical application for treatment of angiogenesis related disorders, the effective amount of active compound employed will range from about 0.01% to about 10%, preferably about 0.05 to about 5%, most preferably about 0.05 to about 3%, by weight of the total composition. Each compound can be used alone, or in combination with the other.

The catechin component of the composition useful in the methods of the invention can be incorporated into any type of vehicle that is appropriate for the intended mode of administration, which will of course depend upon the condition to be treated. The catechins can be formulated for systemic, e.g., oral or parenteral delivery, or can be formulated for topical delivery. Formulation of these active ingredients is achieved by routine methods, such are described in Remington's Pharmaceutical Sciences, $18^{th}$ ed., 1990, the contents of which are incorporated herein by reference.

The utility of the these green tea catechins in inhibiting angiogenesis makes them very useful in the treatment of a broad variety of conditions, the pathology of which is connected with proliferation of blood vessels, or the migration of blood cells. Such conditions include vascularized solid cancerous tumors, which, as proliferating tissues, are heavily reliant on blood vessels to support their growth. Thus, the EGCG/ECG compositions can be used in a method of treatment of neoplastic growth, either topically or systemically. Additionally, EGCG and/or ECG can be used to prevent angiogenesis caused by chronic inflammatory conditions such as rheumatoid arthritis and psoriasis. The EGCG/ECG compositions can also be used in the treatment of diabetic retinopathy.

In a preferred embodiment, the catechins are used topically to treat skin conditions that are angiogenesis-related. Examples of such conditions include inflammatory skin disorders, such as psoriasis, atopic dermatitis, contact dermatitis, skin cancers such as melanoma, or basal or squamous cell carcinoma, spider veins, and undereye circles. In topical application, the active catechin component is added to the chosen vehicle in the amounts indicated above, and typically applied to the skin in an amount of from about 0.1 $\mu g/cm^2$ to 2 $mg/cm^2$ of skin. Depending upon the condition, the composition may be applied on a temporary schedule, until such time as the condition is relieved, or, with chronic conditions, the compositions can be applied chronically, e.g., a safe and effective amount of a composition containing the mixture is applied to prevent development of the symptoms of the angiogenesis-related condition, or to relieve a recurring condition. In all cases, topical application of the composition can be performed from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months -to about ten years, more preferably still from about one year to about five years, which treatment can prevent development of conditions such as undereye shadows and circles, skin inflammation or spider veins.

It may also be desirable to combine other actives with the EGCG/ECG components of the compositions. Examples of other actives that may provide a particular beneficial effect in combination with EGCG or ECG are shark cartilage, phytosphingosine or sphingosine, each of which also has an effect on angiogenesis; skin whiteners, particularly tyrosinase inhibitors, which will supplement the activity of the EGCG/ECG in the treatment of dark circles, to treat or prevent any associated melanization; and antiirritants, to prevent edema that may be associated with any of the treated conditions.

The invention is further illustrated by the following non-limiting examples.

EXAMPLES

Example 1

The ability of green tea catechins to inhibit migration of endothelial cells on a collagen matrix is evaluated in a system modeled after the "Boyden chamber" chemotaxis assay. The membrane separating the two chambers is coated with collagen type IV. The top chamber is loaded with human dermal microvascular endothelial cells(HMVEC-d, 250,000 cells/ml) and 5% bovine serum albumin. The bottom chamber contains vascular endothelial growth factor (VEGF, 100 ng/ml) and 5% BSA. Compositions containing an EGCG/ECG combination (77&:23%) in concentrations of from 0.001 to 1 mg/ml are added to both the top and bottom chambers, and incubated for 6 hours at 37° C.; appropriate vehicle controls are also run. The amount of migrating cells is determined by removing cells remaining on the surface of the membrane by trypsinization, solubilizing the cells embedded in the membrane and quantitating spectrophotometrically with 1% crystal violet at an optical density of 600 nm. The results, shown in FIG. 1, indicate that EGCG/ECG inhibits vessel growth in a dose dependent fashion, at concentrations from about 0.01 to 1 mg/ml.

Example 2

The chorioallantoic membrane(CAM) of fertilized chicken eggs has been shown to provide a vascular network suitable for the analysis of anti-angiogenic activity. To test the in vivo activity of the green tea catechins, ten fertile white leghorn eggs are incubated at 37° C. for 10 days, treated with test sample for 48 hours and evaluated for loss of vasculature compared to controls. On day four, 2.5 ml albumen in removed through a hole drilled at the tip of the egg and then resealed. At this time a rectangular window is cut through the shell directly over the embryo and resealed with tape. On day ten the eggs are removed from the incubator and the chorioallantoic membrane is evaluated for vessel quality; eggs with abnormal or undeveloped membranes are discarded. Test samples over a dose range of 0.01 to 1 mg/ml are pipetted(40 $\mu$l ) onto 13 mm round Thermanox coverslips and allowed to air dry. The coverslip is then placed face down onto the CAM and the eggs are returned for the incubator for 48 hours. Following the 48 hour exposure period the CAM of the eggs are evaluated for three criteria in comparison with untreated controls: egg viability, the number of eggs showing prevention of vessel development, and the extent of the area showing loss of vasculature (e.g., 25–50%, 50–75%, or >75%). Phytosphingosine is used as a positive control (showing 100% inhibition at 2.5 mg/ml). Table 1 shows the results observed with EGCG/ECG, and indicate that EGCG at higher concentrations inhibit angiogenesis in vivo.

TABLE 1

| Sample | Dose | % Eggs with loss of vasculature |
|---|---|---|
| EGCG/ECG | 1.0 mg/ml | 30% (25–50% loss of vasculature) |
| EGCG/ECG | 0.5 mg/ml | 25% (25–50% loss of vasculature) |
| EGCG/ECG | 0.01 mg/ml | 0% |
| phytosphingosine | 2.5 mg/ml | 100% (50–100% loss of vasculature) |

What we claim is:

1. A method of treating an angiogenesis-related, non-neoplastic skin condition comprising applying to the skin a composition containing an effective amount of a catechin selected from the group consisting of epigallocatechin-gallate, epicatechin gallate, and a combination thereof.

2. The method of claim 1 in which the composition comprises epigallocatechin-gallate.

3. The method of claim 1 in which the composition comprises a combination of epigallocatechin-gallate and epicatechin gallate.

4. The method of claim 1 in which the amount of catechin is from about 0.01 to about 10%.

5. The method of claim 1 in which the amount of catechin is from about 0.05 to about 5%.

6. The method of claim 1 in which the amount of catechin is from about 0.05 to about 3%.

7. The method of claim 1 in which the condition is an inflammatory condition.

8. The method of claim 7 in which the condition is psoriasis.

9. The method of claim 1 in which the condition is spider veins or undereye circles.

10. The method of claim 1 in which the composition further comprises an active ingredient selected from the group consisting of an additional angiogenesis inhibitor, a skin whitener, an antiirritant, and combinations thereof.

* * * * *